United States Patent
Eck et al.

(10) Patent No.: US 7,112,695 B2
(45) Date of Patent: Sep. 26, 2006

(54) METHOD FOR THE PURIFICATION OF A CRUDE ACRYLIC ACID MELT

(75) Inventors: Bernd Eck, Viernheim (DE); Dieter Baumann, Walldorf (DE); Jörg Heilek, Bammental (DE); Klaus Joachim Müller-Engel, Stutensee (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/239,849

(22) PCT Filed: Apr. 4, 2001

(86) PCT No.: PCT/EP01/03827

§ 371 (c)(1),
(2), (4) Date: Oct. 1, 2002

(87) PCT Pub. No.: WO01/77056

PCT Pub. Date: Oct. 18, 2001

(65) Prior Publication Data

US 2003/0060661 A1 Mar. 27, 2003

(30) Foreign Application Priority Data

| Apr. 11, 2000 | (DE) | ............................................. 100 17 903 |
| Jul. 28, 2000 | (DE) | ............................................. 100 36 880 |
| Jul. 28, 2000 | (DE) | ............................................. 100 36 881 |
| Aug. 10, 2000 | (DE) | ............................................. 100 39 025 |

(51) Int. Cl.
*C07C 51/42* (2006.01)

(52) U.S. Cl. .................................. 562/600; 562/598
(58) Field of Classification Search ............... 562/512, 562/531, 532, 598, 600
See application file for complete search history.

(56) References Cited

FOREIGN PATENT DOCUMENTS

| DE | 2136396 | 2/1973 |
| DE | 26 06 364 | 1/1977 |
| DE | 37 08 709 | 10/1988 |
| DE | 196 26 839 | 1/1998 |
| DE | 197 40 252 | 3/1999 |
| DE | 198 29 477 | 1/2000 |
| DE | 198 32 962 | 1/2000 |
| DE | 198 33 049 | 1/2000 |
| DE | 198 38 845 | 3/2000 |
| DE | 199 24 533 | 11/2000 |
| DE | 199 26 082 | 12/2000 |

(Continued)

OTHER PUBLICATIONS

Siegbert Rittner et al.: "Die schmelzkristallisation von organischen stoffen und ihre grosstechnische anwendung" Chem.–Ing. Techn., vol. 57, No. 2, pp. 91–102 1985.

(Continued)

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

In a process for the purification of a crude acrylic acid melt, the crude acrylic acid melt is converted, under the action of low temperatures, into a crude acrylic acid suspension consisting of acrylic acid crystals and residual melt, and the acrylic acid crystals of the crude acrylic acid suspension are freed from remaining residual melt in a wash column, the production of the acrylic acid crystals of the crude acrylic acid suspension being carried out in the presence of water, the wash column being a wash column with forced transport of the acrylic acid crystals and the wash liquid used being the melt of acrylic acid crystals purified in the wash column.

47 Claims, 9 Drawing Sheets

FOREIGN PATENT DOCUMENTS

| | | |
|---|---|---|
| EP | 0 253 409 | 1/1988 |
| EP | 0 297 445 | 6/1988 |
| EP | 0 616 998 | 3/1994 |
| EP | 0 648 520 | 4/1995 |
| EP | 0 722 926 | 1/1996 |
| EP | 0 730 893 | 9/1996 |
| EP | 0 776 875 | 6/1997 |
| JP | 07082210 | 3/1995 |
| JP | 11035519 | 2/1999 |
| WO | 98 25889 | 6/1998 |
| WO | 99/06348 | 2/1999 |

OTHER PUBLICATIONS

P.J. Jansens et al.: "The purification process in hydraulic packed–bed wash columns" Chemical Engineering Science, vol. 50, No. 17, pp. 2717–2729 1995.

D. Verdoes et al.: "Improved procedures for separating crystals from the melt" Applied Thermal Engineering, vol. 17, Nos. 8–10, pp. 879–888 1997.

M. Nienoord et al., "Experiences with the TNO–hydraulic wash column" 4. BIWIC 94/Bremen International Workshop for Industrial Crystalization, Bremen Sep. $8^{th}$–$9^{th}$, 1994, University Bremen.

METHOD FOR THE PURIFICATION OF A CRUDE ACRYLIC ACID MELT

BACKGROUND OF THE INVENTION

1. Field of the Invention

The present invention relates to a process for purifying a crude acrylic acid melt which contains, based on its weight, which does not include water present in the crude acrylic acid melt, ≧80% by weight of acrylic acid and, as impurities different from acrylic acid, at least ≧100 ppm by weight of acetic acid and ≧10 ppm by weight of propionic acid, in which the crude acrylic acid melt is converted, under the action of low temperatures, into a crude acrylic acid suspension consisting of acrylic acid crystals and residual melt, the amount by weight of impurities different from acrylic acid in the acrylic acid crystals being less than, and the amount by weight of impurities different from acrylic acid in the residual melt being greater than, the amount by weight of impurities different from acrylic acid in the crude acrylic acid melt, if necessary a part of the residual melt is separated off mechanically from the crude acrylic acid suspension and the acrylic acid crystals of the remaining crude acrylic acid suspension are freed from remaining residual melt in a wash column.

2. Description of the Background

Acrylic acid, either as such or in the form of its salts or its esters, is especially important for the preparation of polymers for a very wide range of applications (e.g. adhesives, superabsorbers, binders).

Acrylic acid is obtainable, inter alia, by catalytic gas-phase oxidation of propane, propene and/or acrolein. These starting gases, as a rule diluted with inert gases, such as nitrogen, $CO_2$ and/or steam, are passed, in the form of a mixture with oxygen at elevated temperatures and, if required, superatmospheric pressure, over transition metal mixed oxide catalysts and are converted by oxidation into a product mixture containing acrylic acid. By condensing the product mixture or by taking up in a suitable absorbent (e.g. water or a mixture of from 70 to 75% by weight of diphenyl ether and from 25 to 30% by weight of biphenyl), basic separation of the acrylic acid from the product gas stream can be achieved (cf. for example EP-A 297 445 and German Patent 2 136 396).

By removal of the absorbent (and, if required, prior desorption of impurities having poor solubility in the absorbent, by stripping, for example, with air) by extractive and/or distillative separation processes (e.g. removal of the absorbent water by distillation, azeotropic distillation or extractive separation of the acid from the aqueous solution and subsequent removal of the extraction medium by distillation) and/or after the use of other separation steps, an acrylic acid is frequently obtained which is referred to here as crude acrylic acid.

This crude acrylic acid is not a pure product. Rather, it contains a range of different impurities typical for the gas-phase catalytic oxidative preparation route. These are in particular propionic acid, acetic acid and low molecular weight aldehydes (typically, the total content of low molecular weight aldehydes in crude acrylic acid to be treated according to the invention is ≧100 ppm by weight, based on the weight of crude acrylic acid calculated as anhydrous; as a rule, the abovementioned aldehyde content is ≦1% by weight), such as acrolein, methacrolein, propionaldehyde, n-butyraldehyde, benzaldehyde, furfurals and crotonaldehyde. Depending on the method of preparation of crude acrylic acid, it may also contain water as a further impurity. Another typical component of crude acrylic acids are polymerization inhibitors. These are added in the course of the separation processes used for the preparation of crude acrylic acid, where they are intended to suppress a possible free radical polymerization of the α,β-monoethylenically unsaturated acrylic acid, which is why they are also referred to as process stabilizers. Dibenzo-1,4-thiazine (PTZ), 4-hydroxy-2,2,6,6-tetramethylpiperidin-1-oxyl(4-OH-TEMPO) and p-methoxyphenol (MEHQ) occupy an outstanding position among the acrylic acid process stabilizers and may be a component of crude acrylic acid either in each case by themselves or in pairs or as a mixture of three substances. Usually, the total amount of polymerization inhibitors contained in crude acrylic acid is from 0.1 to 2% by weight, based on the weight of the crude acrylic acid (the water present in the crude acrylic acid is not included).

Further undesired impurities of acrylic acid present in the condensed phase are the acrylic acid oligomers (Michael adducts) formed by Michael addition of acrylic acid with itself and with the acrylic acid dimers formed therein. While these compounds are usually virtually completely absent from freshly produced crude acrylic acid (usually, their amount by weight is <0.01% by weight, based on the weight of crude acrylic acid calculated as anhydrous), they form therein when said crude acrylic acid is left to stand for a long time. For statistical reasons, the formation of diacrylic acid is of particular importance, whereas the formation of higher acrylic acid oligomers (trimers, tetramers, etc.) takes place only in a minor amount.

The total amount of other byproducts possibly contained in crude acrylic acid is as a rule not more than 10% by weight, based on the weight of the crude acrylic acid calculated as anhydrous.

In this publication, crude acrylic acid is therefore to be understood as meaning in particular that crude acrylic acid which contains, based on its weight calculated as anhydrous, ≧80% by weight of acrylic acid, from ≧100 ppm by weight to ≦15% by weight of acetic acid, from ≧10 ppm by weight to ≦5% by weight of propionic acid, up to 5% by weight of low molecular weight aldehydes, up to 3% by weight of polymerization inhibitors and from 0 to 5% by weight of acrylic acid oligomers (Michael adducts).

The term crude acrylic acid used here thus also comprises in particular that crude acrylic acid which contains, based on its weight calculated as anhydrous, ≧90% by weight of acrylic acid, from ≧100 ppm by weight to ≦5% by weight of acetic acid, from ≧10 ppm by weight to ≦2% by weight of propionic acid, up to 2% by weight of low molecular weight aldehydes, up to 2% by weight of polymerization inhibitors and from 0 to 3% by weight of acrylic acid oligomers (Michael adducts).

Not least, the term crude acrylic acid used here therefore comprises that crude acrylic acid which contains, based on its weight calculated as anhydrous, ≧95% by weight of acrylic acid, from ≧100 ppm by weight to ≦3% by weight of acetic acid, from ≧10 ppm by weight to ≦2% by weight of propionic acid,
up to 2% by weight of low molecular weight aldehydes,
up to 2% by weight of polymerization inhibitors and
from 0 to 2% by weight of acrylic acid oligomers (Michael adducts).

Based on the amount of acrylic acid contained in the crude acrylic acid, the crude acrylic acids frequently contain no water, but in some cases also up to 5% by weight or up to 4% by weight or up to 3% by weight of water.

Of the components, apart from acrylic acid, contained in the abovementioned crude acrylic acids, most prove to be disadvantageous during the use of crude acrylic acid.

If such a crude acrylic acid were used, for example, for the preparation of esters of $C_1$–$C_8$-alkanols and acrylic acid, the corresponding acetic esters and propionic esters would also be formed in secondary reactions, which reduces the yield of desired acrylic esters, based on the amount of alkanol used. If the acrylic esters formed in the presence of low molecular weight aldehydes are used for free radical polymerizations, their content of the low molecular weight aldehydes generally has a disadvantageous effect, for example, in that they influence, for example, the induction time of polymerization reactions, i.e. the period between reaching the polymerization temperature and the actual beginning of the polymerization. Furthermore, they generally influence the degree of polymerization and may also cause discolorations of the polymers.

The abovementioned disadvantages are usually also applicable when the crude acrylic acid is used directly as an acrylic acid source in polymerizations.

Acrylic acid sources to be used for the production of superabsorbers (=materials for absorbing water and based on polyacrylic acid and its salts) are subject in particular to the requirement that they may contain very little diacrylic acid and very little dibenzo-1,4-thiazine, since both components are undesirable either in the production of superabsorbers (in particular dibenzo-1,4-thiazin presents problems owing to its extremely inhibiting effect on free radical polymerizations in the production of superabsorbers) or in the use of the superabsorbers (superabsorbers are used in particular in the hygiene sector (e.g. baby's diapers); the final stage of superabsorber production consists as a rule of a high-temperature surface crosslinking; at the crosslinking temperatures used, copolymerized diacrylic acid will be at least partially cleaved (inverse Michael addition) with formation of monomeric acrylic acid; an increased content of monomeric acrylic acid is however not tolerable in this area of use).

In practice, separation operations involving rectification are used in particular for further purifying crude acrylic acid (cf. for example EP-A 722 926).

The disadvantage of these separation processes is that they require a large amount of energy, in particular for separating off the components having a similar boiling point to acrylic acid (e.g. propionic acid), since the procedure has to be carried out with high reflux ratios and/or with rectification columns having a large number of theoretical plates. Therefore attempts have also already been made, for example, to synthesize acrylic acid free from propionic and/or acetic acid by appropriate adaptation of the gas phase oxidation process (cf. e.g. JP-A 11 35519 and EP-A 253409). Moreover, the thermal stress generally causes undesirable free radical polymerization of the acrylic acid in the case of purification processes involving rectification.

As an alternative, the melt crystallization procedure has been increasingly used in the very recent past for the preparation of pure acrylic acid (cf. for example EP-A 616 998). Very generally, the contaminated crude acrylic acid (melt) is partially solidifed by cooling. Depending on the phase equilibrium, the corresponding acrylic acid crystals have a lower content of impurities than the remaining liquid residual melt. The separation effect described above and determined purely by thermodynamic factors is weakened by the inclusion of liquid during the crystallization process and by the residual melt still adhering to the solid after the solid/liquid separation. For achieving higher purities, a plurality of successive crystallization stages are often therefore necessary, even in the case of eutectic systems, i.e. the crystals obtained in a first crystallization stage are melted again and subjected to a further crystallization step, etc. The disadvantage of such a successive procedure is that, in each stage, the heat of crystallization has to be removed on freezing and supplied again on subsequent melting. This adversely affects the cost-efficiency of separation processes involving crystallization. For economical use of the melt crystallization process, it is therefore of very decisive importance to achieve very high purity of the isolated crystals with very few crystallization stages.

For the purification of crude acrylic acid melts by crystallization, the prior art predominantly recommends layer crystallization processes (cf. for example German Laid Open Application 2,606,364, EP-A 616 998, EP-A 648 520 and EP-A 776875).

In the layer crystallization processes the crystals are frozen in the form of cohesive, thermally adhering layers. The solid/liquid separation is effected by simply allowing the residual melt to flow away. The purified crystals are then melted. In principle, distinction is made between static and dynamic layer crystallization processes.

In the static processes, the crude acrylic acid melt to be purified is introduced, for example, into tube-bundle or modified plate-type heat exchangers and then partially solidifed by slowly lowering the temperature on the secondary side. After the freezing, the residual melt is discharged and then, by slowly increasing the temperature, first more highly contaminated and subsequently less contaminated fractions from the crystal layer are melted until finally the product having high purity is melted. This process is referred to in the literature as sweating. It is true that static crystallization processes achieve a significant purification effect in one crystallization stage in the case of crude acrylic acids. However, the usually low space-time yield in static crystallization processes is disadvantageous since, in static melt crystallization, the heat transport and mass transfer to the deposition surfaces takes place only by free convection.

Typical of the dynamic layer crystallization of crude acrylic acid melts is forced convection of the crude acrylic acid melt. This can be effected by circulating the crude acrylic acid melt by pumping through tubes with full cross-sectional flow (e.g. German Laid Open Application 2,606,364), by adding the crude acrylic acid melt as a trickle film (e.g. EP-A 616 998) or by passing inert gas into a tube filled with melt or by pulsation.

The disadvantage of a purification of crude acrylic acid melts by dynamic layer crystallization is that the purification effect within one crystallization stage with high impurity contents of the crude acrylic melt is unsatisfactory, and it is for this reason that EP-A 616 998 recommends the use of a combination of static and dynamic layer crystallization for purifying crude acrylic acid melts. However, the disadvantage of this procedure is that it necessarily requires a plurality of crystallization stages. A certain improvement can be achieved by using the washing, recommended in DE-A 3 708 709, of the deposited crystal layers with purer melt fractions. Owing to the small specific surface area of the deposited layers however, the wash effect is not completely satisfactory.

EP-A 616 998 includes the possibility of a suspension crystallization for the purification of crude acrylic acid melt by crystallization, but washing of the isolated suspension crystals to remove adhering residual melt is not considered. Instead, a combination with static crystallization stages is recommended, which is unsatisfactory owing to the inevitable multistage nature of the procedure.

In the suspension crystallization process, as a rule a crystal suspension which consists of crystals having a lower impurity content and a residual melt having a higher impurity content is produced by cooling the starting melt containing the impurities. The solid crystals may grow while present directly in suspension or may be deposited as a layer on a cooled wall, from which they are then scratched off and resuspended in the residual melt, i.e. the solids formation can be carried out in cooled stirred kettles, in scraped-surface heat exchangers or in disk crystallizers, as described, for example, in Chem.-Ing.-Techn. 57 (1985) No. 2, 91–102.

Subsequently required separation of the residual melt from the crystal can initially be carried out purely mechanically by pressing off, filtration and/or centrifuging (cf. for example Chem.-Ing.-Techn. 57 (1985) No. 2, 91–102).

The disadvantage of such a procedure with purely mechanical separation of crystals and residual melt is that, owing to the remaining residual melt adhering to the crystals, the purification effect achievable in one separation step is unsatisfactory in the case of crude acrylic acid melts.

The prior application DE-A 19926082 therefore recommends subsequently washing the mechanically removed acrylic acid suspension crystals additionally with a wash liquid containing acrylic acid, the wash liquid used preferably being an acrylic acid melt whose amount by weight of impurities different from acrylic acid is less than the corresponding impurity content of the mechanically isolated suspension crystals to be washed.

The disadvantage of the washing method used in DE-A 19926082 is that its purification effect is not completely satisfactory. This is presumably due in particular to the fact that the contact achieved between crystals to be washed and wash liquid is not completely satisfactory.

It is now generally known that, in the case of a slurry of suspension crystals, separation of suspension crystals and residual melt may also be carried out either exclusively, or after partial mechanical separation (in particular before use of a mechanical wash column) of residual melt, by means of a suitable washing liquid in a wash column in which the wash liquid is passed countercurrently, to the suspension crystals.

In principle, the wash column types are divided (cf. FIGS. 1 to 4) into those with forced transport of the suspension crystal bed and those with gravity transport of the suspension crystals (a detailed description of the different wash column types is to be found, inter alia, in Chem.-Ing.-Techn. 57(1985) No. 2, 91–102, in Chemical Engineering Science 50, 1995, No. 17, 2712 to 2729, Elsevier Science Ltd., in Applied Thermal Engineering 17, (1997) No. 8–10, 879–888, Published by Elsevier Science Ltd., and the citations stated in the abovementioned references). In wash columns with forced transport of the suspension crystal bed, at least one force other than gravitation in the transport direction is used for transporting the suspension crystal bed.

Inside the wash column, the suspension crystals are transported either from top to bottom or from bottom to top. The wash liquid is passed countercurrently to the suspension crystals in the wash column. In the prior publications DE-A 19626839, DE-A 19740252, DE-A 19829477, DE-A 19832962, DE-A 19833049 and DE-A 19838845 inter alia water or aqueous acrylic acid is recommended as wash liquid to be used for crude acrylic acid suspensions. However, the disadvantage of these wash liquids is that, on the one hand, the purification effect is not completed satisfactorily and, on the other hand, they result in considerable acrylic acid losses.

As an alternative to the abovementioned procedure, it is also possible to melt the suspension crystals reaching the wash column in purified form at the end of their transport distance (the mother liquor is removed as a rule in the opposite part of the wash column), to remove only a portion of the resulting purified melt and to recycle the remaining amount of the purified melt as wash melt to the wash column and to do so countercurrently to the suspension crystals fed to the wash column (in this publication, wash columns operated in this manner are to be referred to in the narrower sense as wash-melt wash columns). Depending on the physical characteristics of the crystal suspension to be treated in the wash column, a purification effect may be achieved either on the basis of all or only on the basis of some of the various mechanisms listed below:

Displacement of the residual melt (mother liquor) by the wash melt,

Washing away of the layer of residual melt adhering to the suspension crystals by the wash melt, Diffusion washing of the few/no regions with throughflow between suspension crystals (for example those in contact over large areas) with wash melt, Crystallization of the wash melt, recycled into the wash column, on the suspension crystals fed countercurrently, Sweating of the suspension crystals in contact with the wash melt, Adiabatic recrystallization of the suspension crystals in contact with the wash melt.

The last three of the abovementioned purification mechanisms are to be referred to here as additional purification mechanisms.

According to Chemical Engineering Science 50, (1995) No. 17, 2717–2729, Elsevier Science Ltd., the contribution of the individual purification mechanisms depends, inter alia, on the time of contact between the suspension crystals and the wash melt and on the morphology and composition of the suspension crystals. In principle, none of the abovementioned purification mechanisms can be excluded because, owing to the smaller melting point depression by impurities, the melting point of the purified crystals is higher than the temperature of the still unwashed crystals, which essentially corresponds to the equilibrium temperature of the crude acrylic acid suspension.

In the case of gravity wash-melt wash columns, the suspension crystals are transported along the wash column by gravity countercurrently to the wash melt which has a lower density and hence a lower specific gravity (and therefore ascends in the wash column). A slowly rotating stirrer (usually <0.035 revolutions per second) frequently extends over the entire gravity wash-melt wash column and serves for preventing agglomeration and/or channel formation in the descending crystal bed. The residence time of the suspension crystals in a gravity wash-melt wash column is $\geq 1$ hour (the difference between the density of the liquid phase and that of the solid phase is as a rule $\leq 15\%$).

Furthermore, the lowest porosity within the crystal bed in a gravity wash-melt wash column is usually >0.45, often ≦0.65. The mother liquor leaves the gravity wash-melt wash column usually via an overflow. The advantage of a gravity wash-melt wash column is that its long residence times of the crystals utilize the additional purification mechanisms to a particular extent. According to Applied Thermal Engineering 17, No. 8–10, (1997), 879–888, Elsevier Science Ltd., a weak point of the gravity wash-melt wash column is a requirement for relatively large crystals.

In the case of wash-melt wash columns with forced transport of the suspension crystal bed, a distinction is made for example between pressure columns (also referred to as hydraulic columns), in which the crystals and the wash melt are transported, for example, externally by pumps and/or hydrostatic level and the mother liquor is generally forced out of the wash column via a filter (on the other side of the filters, atmospheric pressure, reduced pressure or superatmospheric pressure may prevail), and mechanical columns having mechanical force transport means for the crystal bed, such as special rams, stirrers, screws, helices or spirals. Mechanical wash-melt wash columns are particularly suitable for purifying crystal suspensions containing little residual melt. The mother liquor is removed in mechanical wash-melt wash columns, as a rule likewise via filters which are present either behind or in the mechanical forced transport means.

Wash-melt wash columns with forced transport of the crystal bed are distinguished by very much shorter residence times of the crystals in the wash column compared with the gravity wash-melt wash column. Said residence time is ≦30 minutes and is as a rule from 10 to 15 minutes, frequently from 2 to 8 minutes. Furthermore, the lowest porosity (=pore volume/total volume) within the crystal bed of a wash-melt wash column with forced transport is usually ≦0.45. According to Chemical Engineering Science 50, No. 17, (1995) 2717–2729, Elsevier Science Ltd., the residence times of the crystals in wash-melt wash columns with forced transport are too short for there to be a significant probability that the additional purification mechanisms will occur.

JP-A 7-82210 discloses a process for the purification of crude acrylic acid by crystallization, in which first a crude acrylic acid suspension is produced from the crude acrylic acid melt in the presence of water by the action of low temperatures, the purpose of the presence of water being to produce the required low temperatures by evaporative cooling. JP-A 7-82210 mentions only in passing that the presence of the water influences the formation of the acrylic acid crystals such that particularly large crystals grow.

In JP-A 7-82210, the crude acrylic acid suspension produced is finally subjected to purification treatment by means of a gravity wash-melt wash column. Although the purification effect achieved in JP-A 7-82210 with one purification stage is satisfactory, the space-time yield achieved is not. JP-A 7-82210 also notes that the presence of the water during the production of the crude acrylic acid suspension has an advantageous effect on the purity of the acrylic acid crystals washed in the gravity wash-melt wash column. The use of a gravity wash-melt wash column is also recommended in EP-A 730893.

For a satisfactory purification of crude acrylic acid by crystallization in one purification stage (in particular for the satisfactory removal of the impurities propionic acid and/or acetic acid) WO 99/06348 recommends first adding a polar organic substance to the crude acrylic acid, then producing an acrylic acid suspension with the action of low temperatures and washing said suspension in a mechanical wash-melt wash column.

The disadvantage of this procedure is that it requires the addition of a polar organic solvent to the crude acrylic acid.

From a paper by M. Nienoord, G. J. Arkenbout and D. Verdoes on Experiences with the TNO-Hydraulic Wash Column" at the 4th BIWIC 94/Bremen International Workshop for Industrial Crystallization, Bremen, Sep. 8th –9th, 1994, at the University of Bremen, Ed.: J. Ulrich, it is known that hydraulic wash-melt wash columns are suitable in principle for purifying acrylic acid suspensions. However, the abovementioned citation contains no information on the composition of the acrylic acid suspension or on its preparation.

In view of the abovementioned prior art, it is an object of the present invention to provide an improved process for the purification of crude acrylic acid melts which, on the one hand, is capable of providing acrylic acids of high purity and with a high space-time yield in only one purification stage and, on the other hand, requires no prior addition of a polar organic solvent to the crude acrylic acid, in particular for satisfactory removal of propionic and/or acetic acid.

SUMMARY OF THE INVENTION

We have found that this object is achieved by a process for purifying a crude acrylic acid melt which contains, based on its weight, which does not include water present in the crude acrylic acid melt, ≧80% by weight of acrylic acid and, as impurities different from acrylic acid, at least ≧100 ppm by weight of acetic acid and ≧10 ppm by weight of propionic acid, in which the crude acrylic acid melt is converted, under the action of low temperatures, into a crude acrylic acid suspension consisting of acrylic acid crystals and residual melt, the amount by weight of impurities different from acrylic acid in the acrylic acid crystals being less than, and the amount by weight of impurities different from acrylic acid in the residual melt being greater than, the amount by weight of impurities different from acrylic acid in the crude acrylic acid melt, if necessary a part of the residual melt is separated off mechanically from the crude acrylic acid suspension and the acrylic acid crystals of the remaining crude acrylic acid suspension are freed from remaining residual melt in a wash column, wherein a) the production of the acrylic acid crystals of the crude acrylic acid suspension is effected in the presence of from 0.20 to 10% by weight, based on the weight of the acrylic acid contained in the crude acrylic acid melt, of water, b) the wash column is a wash column with forced transport of the acrylic acid crystals and c) the wash liquid used is the melt of acrylic acid crystals purified in the wash column.

DETAILED DESCRIPTION OF THE PREFERRED EMBODIMENTS

Figure 1:
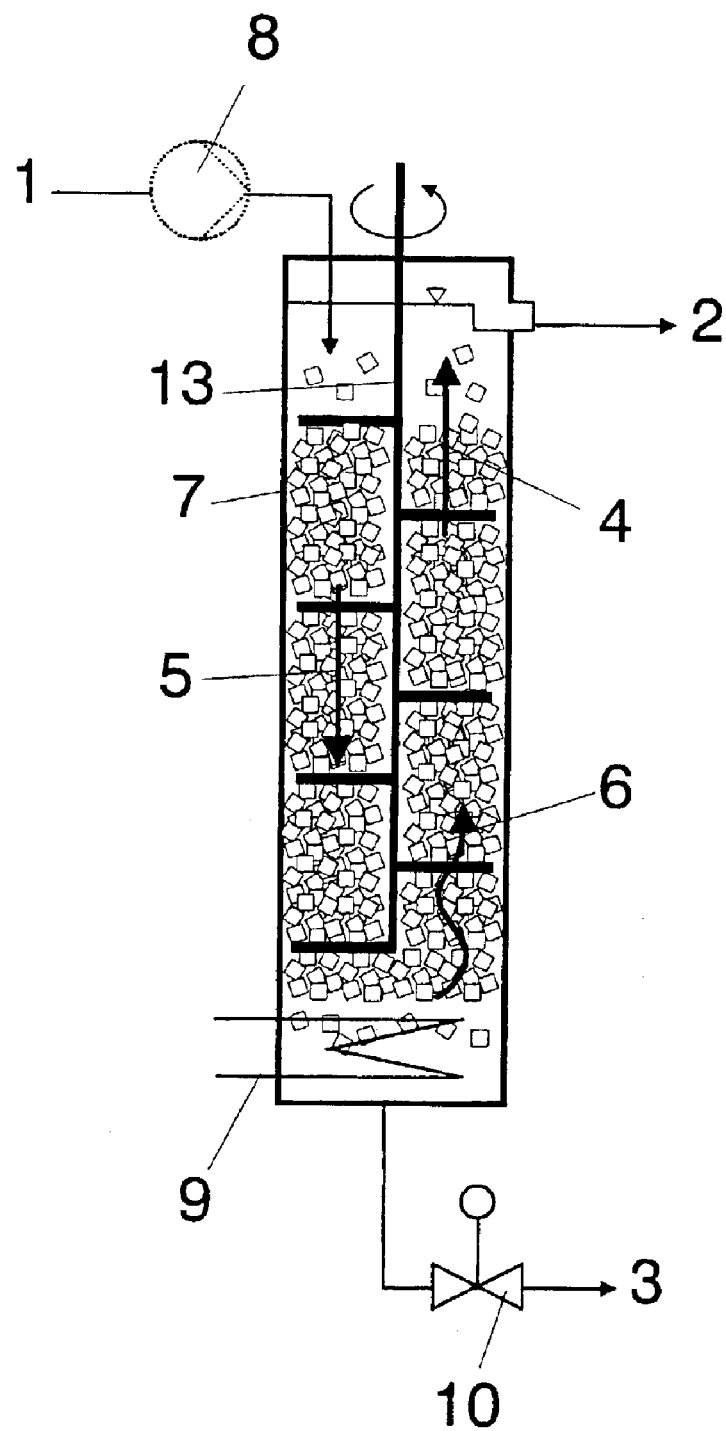
FIG. 1 shows a wash column with a gravity bed.

In principle, the novel process is suitable for all crude acrylic acids mentioned in this publication.

In all cases, the production of the acrylic acid crystals of the crude acrylic acid suspension can be carried out in the presence of from 0.20 to 10 or from 0.40 to 8 or from 0.60 to 5 or from 0.60 to 3 or from 0.60 to 2 or from 0.75 to 1.5% by weight, based on the weight of the acrylic acid contained in the crude acrylic acid, of water.

The crude acrylic acid can deliberately have been prepared so that it contains this amount of water as a result of the preparation. Usually, however, the preparation results in crude acrylic acid which is essentially or completely free of water. In these cases or in cases where the amount of water contained in the crude acrylic acid as a result of the preparation is unsatisfactory, it is of course possible, according to the invention, to bring the water content to the desired level by adding water before the preparation of crude acrylic acid suspensions.

In the preparation of the crude acrylic acid suspension required according to the invention, the solid crystals can be produced in such a way that they are present directly in suspension. However, it is of course also possible to deposit them as a layer on a cooled wall, from which they are subsequently scraped off and resuspended in the residual melt.

This means that, according to the invention, the formation of the solid can be carried out in cooled stirred kettles, in scraped-surface heat exchangers or in disk crystallizers, as described, for example, in Chem.-Ing.-Techn. 57 (1985) No. 2, 91–102.

Very generally, all suspension crystallizers which are stated in the publications mentioned as prior art in this publication are suitable for the novel process for the preparation of the crude acrylic acid suspension.

In particular, the following suspension crystallizers of the companies below can be used as suspension crystallizers:

| Suspensions crystallizer | Company |
| --- | --- |
| Cooling disk crystallizer | Goudsche Maschinefabrik BV, (NL) |
| Scraped cooling crystallizer | Richard M. Armstrong (Scotland) |
| Forced-circulation crystallizer with external heat exchanger | Swenson, Messo Chemietechnik (DE and SE) |

The suspension crystallizers can be operated with refrigerant and crude acrylic acid being fed both cocurrently and countercurrently. The latter is the rule.

As a rule, the acrylic acid crystals of the crude acrylic acid suspension to be produced according to the invention have a cuboid geometry. The ratios of the dimensions of the abovementioned geometrical bodies are frequently as follows: L(length):W (width):H (height)=1 to 5:1:1. The length L is frequently from 10 to 100 μm, in many cases from 100 to 800 μm, or up to 400 μm.

On the way from the crystallizer to the wash column, it is usually expedient to homogenize the crystal suspension (for example by stirring and/or by means of suitable pumps).

Wash-melt wash columns which are suitable according to the invention and may be used are both hydraulic wash columns, (for example that of the TNO Institute in Apeldoorn, The Netherlands (cf. Applied Thermal Engineering 17, No. 8–10, (1997), 879–888, or Chemical Engineering Science 50, No. 17, (1995) 2717–2729, Elsevier Science Ltd., or 4th BIWIC 94/Bremen International Workshop for Industrial Crystallization, Bremen, Sep. 8th –9th, 1994 at the University of Bremen, Ed.: J. Ulrich, or Trans. I. Chem. E, 72, Part A, September 1994, pages 695 to 702, and Applied Thermal Engineering 17, Nos. 8–10, (1997), 879–888, Elsevier Science Ltd.)) and mechanical wash columns (for example that from Niro, Process Technology B.V., Hertogenbosch, The Netherlands).

According to the invention, very generally all those wash-melt wash columns with forced transport of the acrylic acid crystals which are mentioned in the publications cited as prior art in this publication can be used. The publications Chem.-Ing.-Techn. 57 (1985) No. 2, 91–102, and Chem.-Ing.-Techn. 63 (1991), No. 9, 881–891, and WO 99/6348 may be mentioned by way of example.

Those wash-melt wash columns with forced transport which are described in patents of TNO or Niro or other companies are also particularly advantageous according to the invention (cf. for example EP-A 97405, U.S. Pat. No. 4,735,781, WO 00/24491, EP-A 920894, EP-A 398437, EP-A 373720, EP-A 193226, EP-A 191194, WO 98/27240, EP-A 305 316 and U.S. Pat. No. 4,787,985). It is not important according to the invention that the TNO and Niro systems are frequently designed primarily for removing water from liquid foods or for extractions.

The crude acrylic acid suspension to be produced according to the invention can be produced with an acrylic acid crystal content of from 10 to 80, frequently from 20 to 60, and in many cases from 30 to 50, % by weight, based on the total weight of the crude acrylic acid suspension.

The crude acrylic acid suspensions thus produced, either as such or only after a part of the residual melt contained in them has been mechanically removed, can be subjected to the novel wash column process. Suitable means for mechanical separation of the crystal phase are presses, sieves, centrifuges and filters. For example, belt filters, drum filters, Seiner screws and curved sieves can be used. Of course, decanting and sedimentation techniques are also suitable. Frequently, the mechanical separation of the crystal phase from the crude acrylic acid suspension is carried out, according to the invention, in such a way that the crystal phase is still dripping wet with residual melt. The acrylic acid crystal phase separated from the crude acrylic acid suspension may still contain from 5 to 30, or up to 10% by weight, based on the total weight of the acrylic acid crystal phase and residual melt, of residual melt. For the novel further purification of such dripping wet acrylic acid crystal phases, mechanical wash-melt wash columns are particularly suitable.

According to the invention, it is important that, in order to achieve a satisfactory purification effect, it is not necessary to subject a hereinabove mechanically isolated crystal phase to resuspension before its further purification in a wash-melt wash column with forced transport, as recommended, for example in WO 98/25889. Of course, such a resuspension could however be carried out before the use of the novel wash column purification step.

Frequently, the novel wash-melt wash column purification step is carried out in such a way that the difference between the temperature of the crude acrylic acid suspension fed to the wash column and that of the wash melt recycled to the wash column (i.e. the temperature difference) is from 2 to 15° C., frequently from 2 to 10° C. or from 2 to 4° C.

According to the invention, it is surprising that, in spite of the very much shorter residence time of the acrylic acid crystals of frequently from 5 to 25, often from 10 to 15 and in many cases from 12 to 14, or from 2 to 8 minutes, in the wash-melt wash columns to be used according to the invention and with forced transport, a purification effect is achieved which is equivalent to that in a gravity wash-melt wash column. This is due to the particular crystal characteristics of the acrylic acid crystals, which have these characteristics owing to their production in the presence of water. In addition, purified acrylic acid appears to extract from such crystals, in a particularly effective manner, in particular the acetic and/or propionic acid included therein, which is also likely to be the reason for the excellent success of the novel procedure. The novel process is also striking in that it is capable of separating the low molecular weight aldehydes such as furfurals, from the crude acrylic acid in an excellent manner.

According to the invention, it is important that the novel process requires no addition of a polar organic substance to the crude acrylic acid before the preparation of the crude acrylic acid, as considered to be essential by WO 99/06348.

However, the novel procedure can of course also be used together with the procedure of WO 99/6348. In this case, the preparation of the crude acrylic acid suspension is carried out both in the presence of water and after addition of a polar organic liquid to the crude acrylic acid to be purified.

The novel process can of course also be carried out in such a way that the crude acrylic acid suspension to be washed according to the invention is the result of a fractional crystallization, for example of a fractional suspension crystallization. However, it is important according to the invention that such a fractionation is not essential for a successful purification.

Of course, the crystallization required according to the invention can be effected by indirect cooling, for example jacket cooling, and/or by direct cooling (for example, use of a coolant, such as $CO_2$ and/or propane, and/or evaporation of water).

It is particularly advantageous to apply the novel process to a crude acrylic acid which is produced by the procedure disclosed in DE-A 19909923.

Of course, the novel procedure can also be used several times in succession. It is also possible to recycle the residual melt (mother liquor) removed from the wash column in the novel process to the process for the preparation of crude acrylic acid, for example to the column for the fractional condensation of the reaction gas mixture of the gas-phase oxidation, as recommended at various points in the literature.

Figure 5:
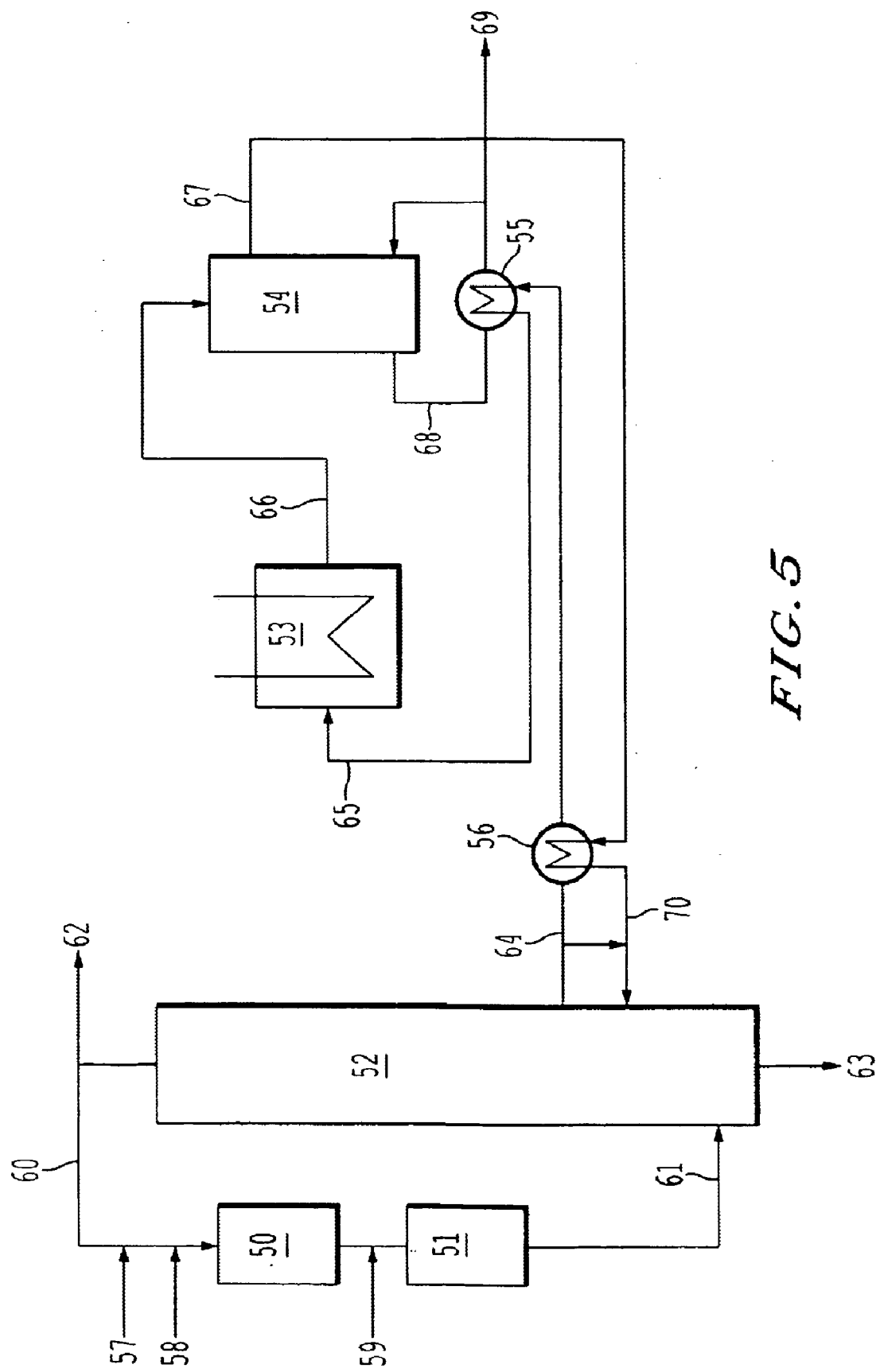
FIG. 5 shows a process scheme for the gas phase oxidation of propene to acrylic acid and processing of the crude acrylic acid produced.

For example, the novel procedure can be integrated as follows into the processes for the preparation of acrylic acid which are published in DE-A 19909923, DE-A 19924533, DE-A 19924532, DE-A 19833049, DE-A 19740253, DE-A 19740252 and in particular DE-A 19627847 (the schematic integration is shown in FIG. 5 attached to this publication, to which the following addresses relate).

Thereafter, propene or propane is subjected in an oxidation zone to heterogenously catalyzed gas-phase oxidation with the molecular oxygen at elevated temperatures to give acrylic acid (for example, propene (8) and atmospheric oxygen (9, 10) fed into reaction recycled gas (11) having a low acrylic acid content, and the propene is oxidized in the gas phase at elevated temperature by introducing a catalysis in two successive oxidation stages (1, 2) over multimetal oxide materials containing Mo, Bi and Fe (first stage) and Mo and V (second stage).

The reaction gas (12) arriving from the oxidation zone and enriched in acrylic acid is subjected (for example in a multistage condensation column (3)) to a fractional condensation (the column is generally operated adiabatically), in which an acrylic acid-rich liquid fraction (typically containing from 0.2 to 10% by weight, based on acrylic acid present, of water) is formed. The water content of the crude acrylic acid can be established, for example, by recycling some of the dilute acid solution obtained at the top of the condensation column, inside and/or outside the condensation column, to the crude acrylic acid removal tray.

This crude acrylic acid (15) is removed (for example via a side take-off of the condensation column) and is fed for further purification (preferably without prior addition of foreign substances) to a suspension crystallization purification stage. The waste gas stream (13) which, in addition to air components, contains substantially water and other low boilers is separated off from the gas stream having a low acrylic acid content and emerging at the top of the condensation column. At the bottom of the condensation column, a high boiler-rich liquid fraction (14) is taken off.

Waste gas stream and high boiler fraction can be further treated as described in the abovementioned publications. In the crystallizer (4), acrylic acid crystals are precipitated from the preferably precooled crude acrylic acid (16) by withdrawal of heat and suspension which contains, for example, from 20 to 40% of its weight of acrylic acid crystals in the remaining mother liquor is thus produced.

This suspension (17) is fed in unchanged form, preferably as such, to the relevant wash-melt wash column, in which a substantially complete separation of the acrylic acid crystals from their mother liquor is carried out by filtration and countercurrent washing.

The washed acrylic acid crystals are melted in a melt circulation (19). A part (in the case of a hydraulic wash column, typically from 20 to 30% by weight) of this melt is used in the wash column as a wash medium for the countercurrent washing and, in unfavorable cases, leaves the wash column together with the mother liquor (18). The other part of the melt is removed as comparatively pure acrylic acid.

The precooling of the crude acrylic acid (15) is expediently effected by an indirect method in the heat exchangers (6) and (7). The heat removed is used in an advantageous manner for melting the acrylic acid crystals in the melt circulation (19, 6) and expediently for preheating mother liquor (18) recycled to the condensation column (3).

The following compositions are typical of the entering and emerging streams as described:

| | | |
|---|---|---|
| Crude acrylic acid (15/16): | 97.2% | by weight of acrylic acid |
| | 4000 ppm | by weight of acetic acid |
| | 619 ppm | by weight of propionic acid |
| | 5000 ppm | by weight of furfural |
| | 703 ppm | by weight of benzaldehyde |
| | 1500 ppm | by weight of maleic anhydride |
| | 200 ppm | by weight of phenothiazine |
| | 1.5% | by weight of water |
| Mother liquor (18): | 96.4% | by weight of acrylic acid |
| | 6000 ppm | by weight of acetic acid |
| | 744 ppm | by weight of propionic acid |
| | 7000 ppm | by weight of furfural |
| | 925 ppm | by weight of benzaldehyde |
| | 2000 ppm | by weight of maleic anhydride |
| | 263 ppm | by weight of phenothiazine |
| | 1.9% | by weight of water |
| Purified acrylic acid: | 99.7% | by weight of acrylic acid |
| | 1030 ppm | by weight of acetic acid |
| | 225 ppm | by weight of propionic acid |
| | 7 ppm | by weight of furfural |
| | 1 ppm | by weight of benzaldehyde |
| | 2 ppm | by weight of maleic anhydride |
| | <1 ppm | by weight of phenothiazine |
| | 0.1% | by weight of water. |

In other words, the process route involving heterogeneously catalyzed gas-phase oxidation of propene or propane to an acrylic acid-containing product gas mixture, fractional condensation of this product gas mixture with removal of a crude acrylic acid containing from 0.2 to 10% by weight of water (based on acrylic acid present), one-stage suspension crystallization of the crude acrylic acid to give a crystal suspension containing from 20 to 40% of its weight of acrylic acid crystals and subsequent washing of the crystal suspension according to the invention in a wash column with forced crystal bed transport usually permits, with minimum apparatus costs, the preparation of an acrylic acid quality which contains ≧99.5% of its weight of acrylic acid.

Suitable cooling media for all indirect cooling discussed in this publication are mixtures of ethylene glycol and water or of methanol and water.

Wash columns suitable according to the invention for the integration described are, as stated above, in particular two types:
A) Wash columns with hydraulic transport of the crystal beds.
B) Wash columns with mechanical transport of the crystal beds.

The crystal volume fraction in the crystal bed generally reaches >0.6 in both wash column types. As a rule, values from 0.7 to 0.75 are reached. Some of these wash column types are to be presented below.

A) Suitable Wash Columns with Hydraulic Transport of the Crystal Bed

Figure 6:
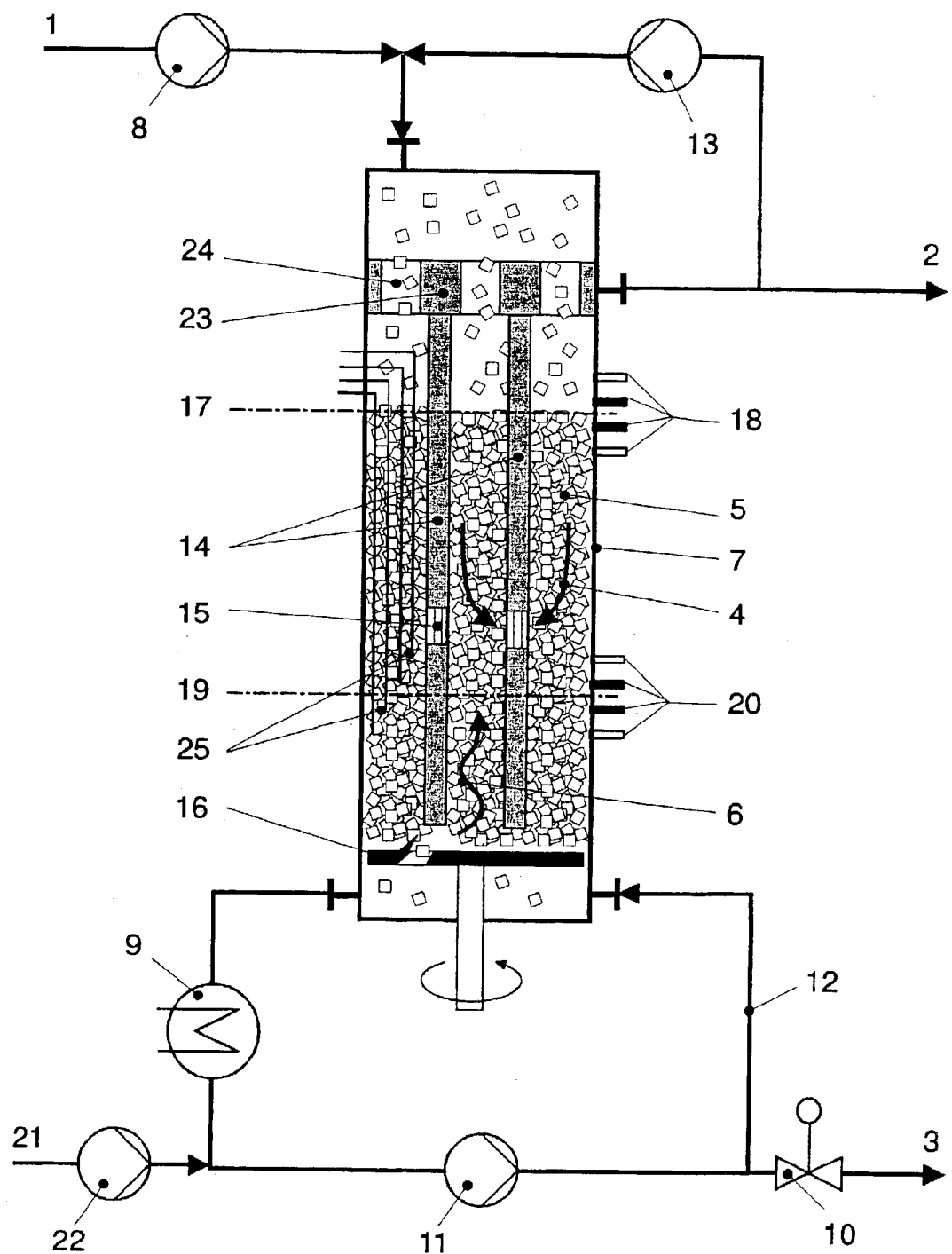
FIG. 6 shows a hydraulic wash column for processing of acrylic acid crystals.

FIG. 6 attached to this publication schematically shows the design of a hydraulic wash column suitable for the integration described. The suspension (1) of acrylic acid crystals in mother liquor, taken off from the suspension crystallizer, is fed by means of a pump (8) and/or via hydrostatic level under superatmospheric pressure into the wash column (7). A fluid register which performs two functions is arranged in the upper part of the wash column. The suspension is distributed over the cross section of the wash column via passages (24) from the upper to the lower part of the column. The cohesive interior of the fluid register (23) serves as a collector for the liquids removed (mother liquor and wash liquid (2)). Drainage pipes (14) are mounted below in the fluid register (they have a constant cross section within the concentration zone; viewed in the direction of the suspension feed, this is the zone up to the first filter) and are connected to the interior (23). The drainage pipes are provided, at a defined height, with at least one conventional filter (15) each, through which the mother liquor (4) is removed from the wash column (the mother liquor may be under atmospheric pressure, superatmospheric pressure or reduced pressure). A compact crystal bed (5) forms. The crystal bed is transported by the force resulting from the hydraulic flow pressure loss of the mother liquor past the filters into the wash zone below the filters. The recycling of a part of the mother liquor into the column by means of the pilot pump (13) permits regulation of this transport force. Variations in the crystal content in the suspension fed in or changes in the crystal size distribution, which substantially influence the flow pressure loss, can thus be compensated. Such variations are evident from the change in position of the filtration front (17), which can be determined by optical position detectors (18).

At the lower end of the wash column the crystals are removed from the crystal bed by means of a rotor blade (16) and are resuspended in pure product melt, which may be overinhibited with p-methoxyphenol (MEHQ). This suspension is transported in a melt circulator (12) via a heat exchanger (9), by means of which the heat required for melting the crystals is introduced indirectly. From about 70 to 80% by weight, in advantageous cases (for example with pronounced recrystallization) even-from >80 to 100% by weight, of the molten crystals are removed as pure product (3) from the melt circulation. The amount of pure product removed is set by means of the product control valve (10).

The remaining part of the product melt flows as wash medium (6), in a direction opposite to the direction of transport of the crystal bed, to the filters (15), with the result that countercurrent washing of the crystals takes place in the wash zone. The purification of the crystals is based substantially on the displacement and dilution of the mother liquor in the voids of the crystal bed by wash liquid. The dilution effect is based here on mixing in the voids between the crystals, through which flow takes place, and diffusion at the contact points where there is no through-flow, or at the surface-near flow boundary layer of the crystals.

In steady-state operation, the wash front (19) is established at a defined height in the wash zone. The concentration transition between mother liquor concentration (above wash front) and pure melt concentration (below the wash front) takes place at the height of the wash front. The wash front (19) must be positioned above the rotor blade (16) in order to achieve an adequate purification effect at a minimum height. The position (19) is established as a dynamic equilibrium of transported crystal mass flow (5) and countercurrent wash medium flow (6). The amount of wash medium results from the amount of pure product removed.

With comparatively good purity of the crude acrylic acid, the crystallization temperature in the suspension crystallizer is only from 3 to 4° K below the melting point of the pure product. In the region of the wash front, recrystallization of the wash liquid therefore occurs only to a small extent on temperature equilibration of the cold crystals with the wash liquid. This limits the recovery of the wash melt by recrystallization as well as the reduction of the porosity of the crystal bed below the wash front by recrystallization. Such low porosity of the crystal bed would reduce the amount of wash medium required as well as recovery by recrystallization.

With good purity of the crude acrylic acid, it is furthermore expedient to feed the storage stabilizer methoxyphenol (MEHQ) into the melt circulation (12) of the wash column. For this purpose, the MEHQ, dissolved in pure product, is added by means of a metering pump (22) to the relatively warm melt circulation for stabilization. MEHQ passes, together with the removed mixture of mother liquor and wash melt (2) into the column used for the fractional condensation (FIG. 5, number 3) and stabilizes said column.

Figure 7:
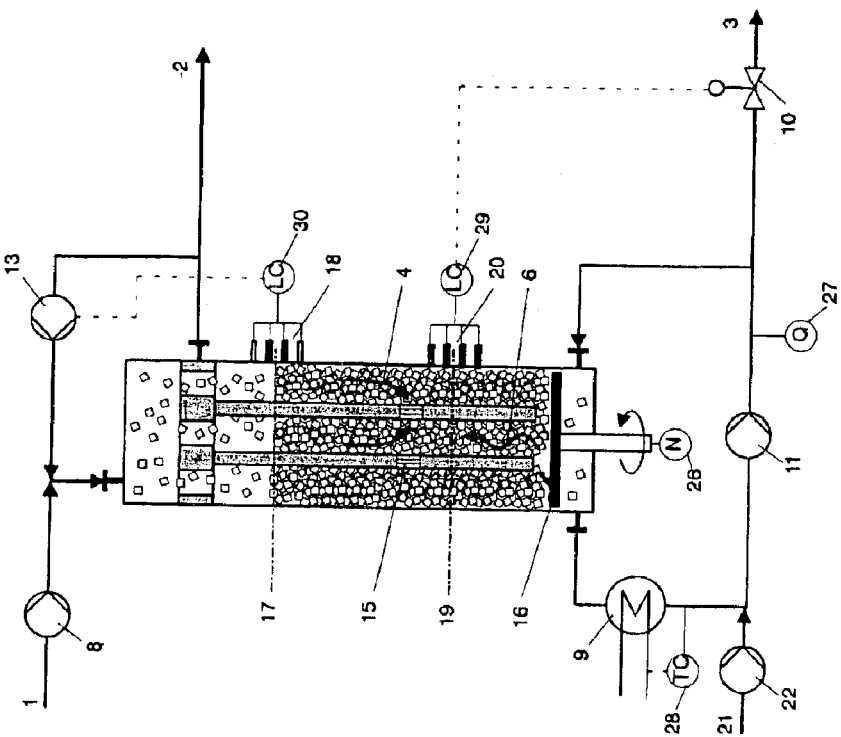
FIG. 7 shows a device for the regulation of the filtration front of a hydraulic wash column.

In order to ensure stable operation of the hydraulic wash column in the context of a defined space-time yield and a constantly good purification effect, it is expedient to compensate external disturbance variables, such as variations in the amount of suspension,
change of crystal content in the suspension,
variation of the crystal size distribution and
concentration variations in the feed and/or in the mother liquor by regulating
a) the filtration front (FIG. 6, number 17),
b) the specific amount of wash medium (FIG. 6, number 6) and
c) the heat of fusion (FIG. 6, number 12).

a) Regulation of the Filtration Front (the Addresses Used Relate to FIG. 7 Attached to this Publication)

A constant position of the filtration front ensures that the external mass balance of the wash column is maintained at all times. Its position is preferably determined by four optical reflection sensors (18) which are mounted at defined heights in the column wall. Detection of position by means of a line camera through a corresponding window in the column wall or radiometric reflection methods are suitable as further possible methods of detection. The reflection methods are based on the fact that the intensity of the reflected radiation is dependent on the position of the bed edge. The line camera shows the complete concentration and wash zone in a vertical line. The filtration front is evident from a change of intensity in the line signal. The recycled amount of mother liquor is regulated (30) and can be varied by the pilot pump (13), for example by a change of speed. If the crystal bed rises, the quantity of control current is increased (the pressure drop consequently increases); if the bed falls, it is reduced. The quantity of control current is preferably changed not abruptly but steadily, for example linearly as a function of time.

b) Regulation of the Specific Amount of Wash Medium (of the Wash Front)

The specific amount of wash medium is the amount of wash medium which is based on the pure product stream effectively leaving the wash column and which is to be applied for achieving a defined separation effect. The following addresses relate to FIGS. 7 to 9 attached to this publication.

Control Concept 1:
Setting the Wash Front (19) Below the Filters (15)

The wash front (19) is set by regulating (number 29 in FIG. 7 or number 31 in FIG. 8) the amount of wash medium via the product valve (10) to a defined position between filter (15) and rotor blade. In this procedure, the separation task is performed with minimum use of the wash medium.

Figure 8:
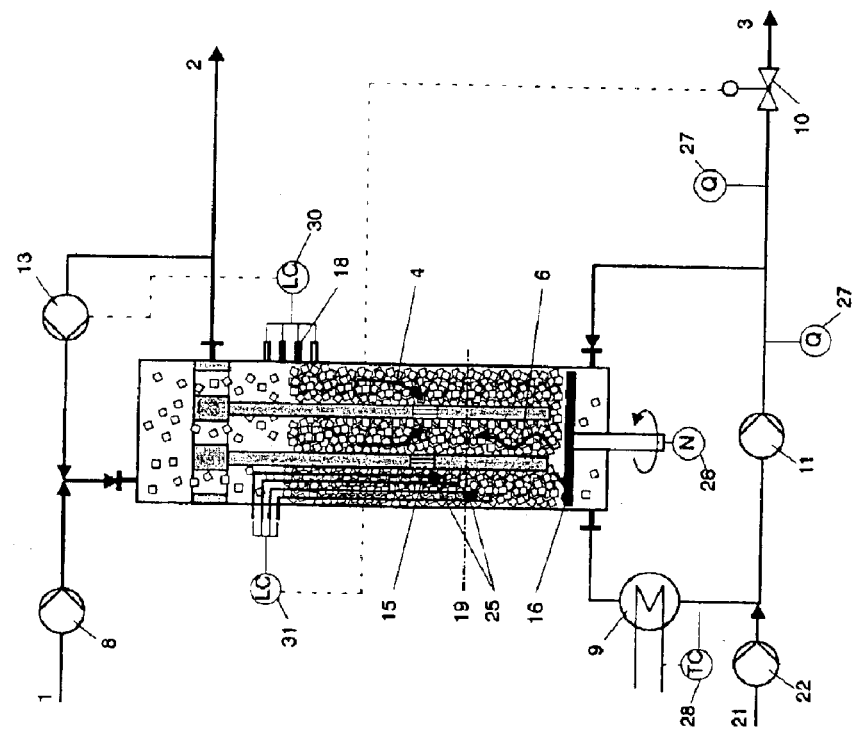
FIG. 8 shows a device for the regulation of the specific amount of wash medium of a hydraulic wash column by optical reflection sensors.

The detection of the wash front can be effected, for example, by four or more optical reflection sensors (FIG. 7, number 20) or preferably by four or more temperature sensors arranged in the crystal bed (FIG. 8, number 25).

Control Concept 2:
External Balancing of the Specific Amount of Wash Medium

Figure 9:
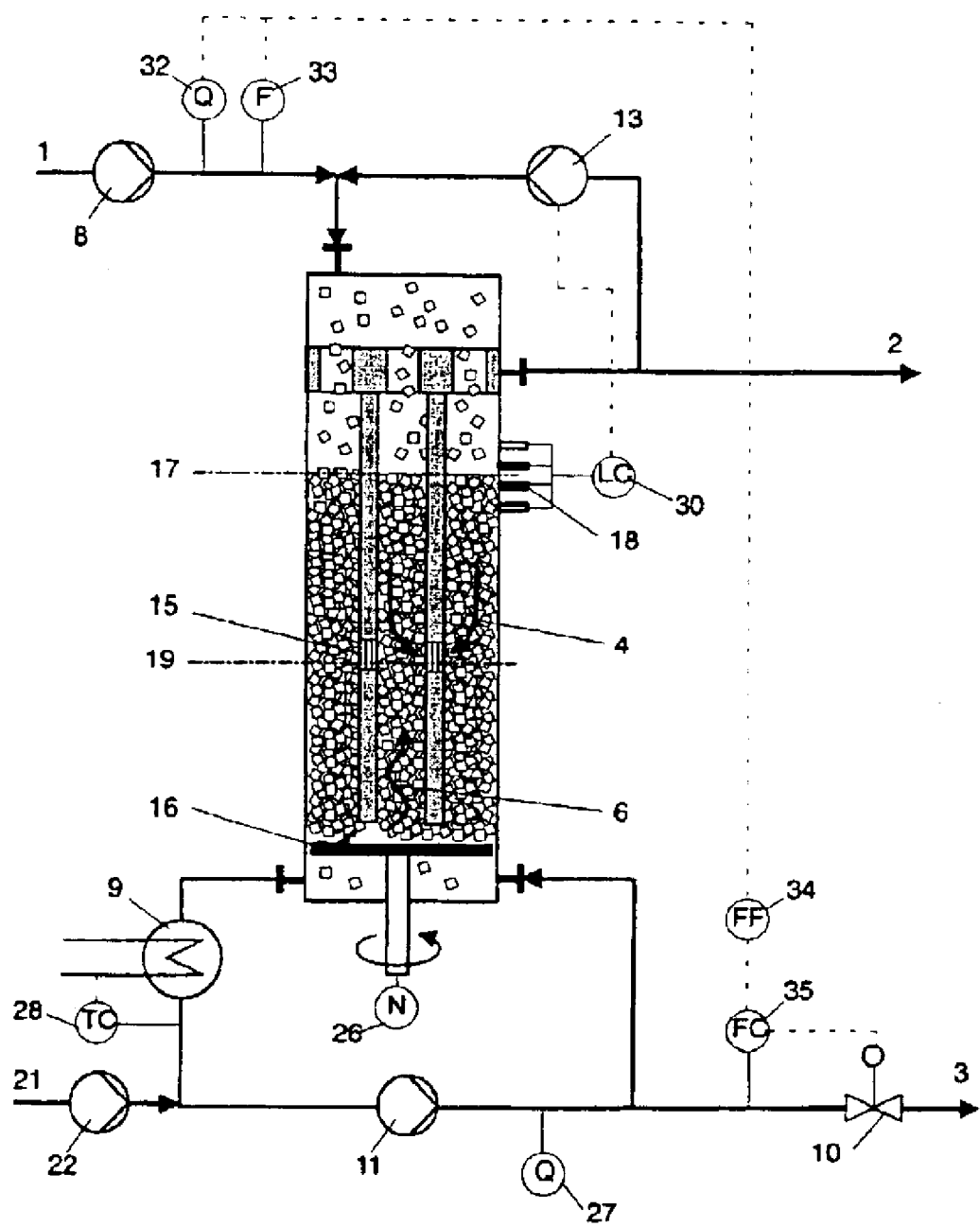
FIG. 9 shows a device for the regulation of the specific amount of wash medium of a hydraulic wash column by use of an optical extinction sensor.

The specific amount of wash medium is set as a defined ratio to the amount of crystals fed in, which ratio is to be determined empirically. The ratio must be chosen to be sufficiently large to guarantee that a wash front is established. This is achieved by setting an excess of wash medium (based on control concept 1). The wash front (19) is established at the filter (in the region of the lower edge of the filter to the middle of the filter) (cf. FIG. 9, to which the following addresses also relate). The regulation of the ratios (34) is based on the measurement of the suspension mass flow (33), or the crystal content in the suspension (32) and of the amount of crude acrylic acid removed. The amount of wash medium is set indirectly by the amount of pure acrylic acid product removed (33)=amount of crystals–amount of wash medium. For maintaining and controlling the purification effect, for example a quality (27) of the pure acrylic acid product can be monitored. For this purpose, the measurement can be effected by means of an optical extinction sensor in the spectral range of 450 nm directly in the product line or in the bypass (it detects a coloration presumably due to phenothiazine still present). The quality measurement is effected in the melt circulation line and can thus also be used for starting up the wash column. The control concept 2 is simpler to implement but has a higher wash medium requirement compared with control concept 1.

c) Regulation of the Heat of Fusion (the Addresses Relate to FIGS. 7 to 9)

The introduction of the correct quantity of heat into the melt circulation for melting the crystals is ensured by regulation of the temperature of the pure acrylic acid product (28) after the heat exchanger (9). The temperature in the melt circulation may be from about 1 to 5° K above the melting point of the pure acrylic acid product.

The rotor blade (26) is expediently operated at a fixed speed (from 20 to 60 revolutions per minute).

Further information on the regulation of the filtration front using a line camera and on the external balancing of the specific amount of wash medium in a hydraulic wash column is to be found in DE-A 10 036 880 and DE-A 10 036 881.

The other regulations of the front and heat of fusion which are to be considered during operation of a hydraulic wash column according to the definition are described in detail, for example in Trans I Chem E, Vol. 72, Part A, September 1994 and in the dissertations Hydraulic Wash Columns, Sold-Liquid Separation in Melt Crystallization by Lianne van Oord-Knol, Technical University of Delft, Jun. 13, 2000 (ISBN 90-805709-1-5) or Fractional Suspension Crystallization of Organic Compounds by Pieter Johannes Jansens, Technical University of Delft, Apr. 5, 1994 (ISBN 90-370-0097-5).

Start-up Procedure of the Hydraulic Wash Column (the Addresses Relate to FIG. 6)

The suspension (1) arriving from the crystallizer is fed into the wash column (7) under superatmospheric pressure by means of a pump (8) or by hydrostatic pressure. Arranged in the wash column are one or more drainage pipes (14) which are provided at a defined height with at least one filter (15) each, through which the mother liquor (4) is removed from the wash column. When the wash column is started up only mother liquor is first removed and the crystals remaining in the wash column form a fixed bed whose porosity is from about 30 to 40% by volume. The pores between the crystals are completely filled with mother liquor. Once a defined bed height (17) has been reached, the rotor blade

(16) arranged at the lower end of the wash column is switched on, the task of which is to remove the crystal bed uniformly at its lower end. The crystals scraped off pass below the rotor blade into a melt circulation (12) in which a circulation pump (11) and a heat exchanger (9) are arranged. The heat required for melting the crystals is supplied by the heat exchanger (9). In order to ensure the driving temperature gradient required for the melting process, the product temperature at the outlet of the heat exchanger (9) is set at from about 1 to 5° K above the melting point of the pure product. The melt is initially a mixture of molten crystals and mother liquor, having a mixing ratio corresponding to the porosity of the crystal bed. The product control valve (10) initially remains closed and, since suspension is fed in continuously, the melt (6) having a lower density inevitably flows in a direction opposite to the downward-moving crystal bed, toward the filter. As a result, washing of the crystals takes place.

The impure mother liquor transported into the pores of the crystal bed is washed out countercurrently by the purer melt, and the wash liquid (6) escapes through the filter (15). Consequently, the purity of the crystal bed in the wash zone, the region between the rotor blade (16) and the filter (15), now increases steadily. Once the product purity (for measurement cf. FIG. 7, number 27) reaches its highest level, the product control valve is opened to such an extent that from about 70 to 80% by weight, in favorable cases from >80 to 100% by weight, of melt leaves the wash column as pure product and only the remaining part (frequently from about 20 to 30% by weight) is used as wash medium (6) in the manner described and flows toward the filter. The wash column is now in steady-state operation.

Figure 10:
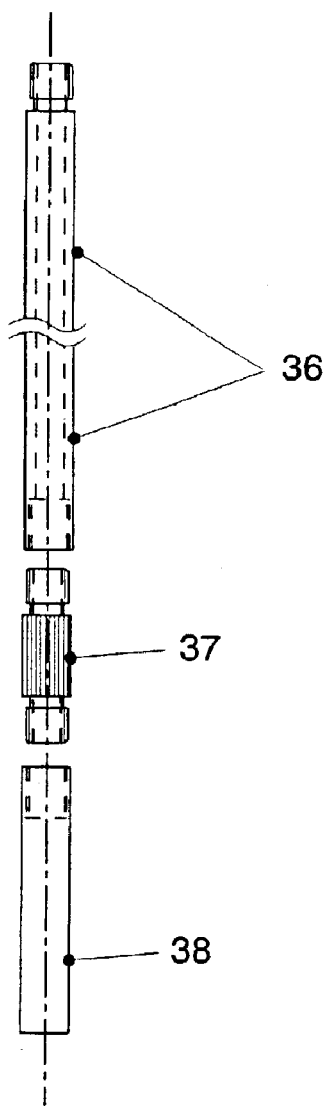
FIGS. 10 and 11 each show the design of a drainage pipe embodiment.
Figure 11:
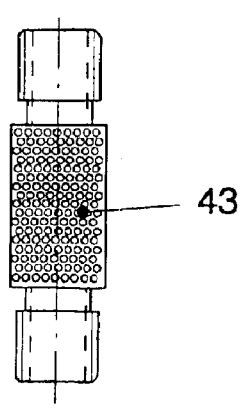

Design of the Drainage Pipes (cf. Attached FIGS. 10 and 11)

The drainage pipes serve for removing the mother liquor and the wash liquid from the crystal bed. All drainage pipes in the hydraulic wash columns are usually of the same design. They are expediently composed of a plurality of construction elements which perform the following functions:

liquid transport filtration heat insulation heat conduction displacement

In a simple version (FIG. 10), the drainage pipe consists of the discharge pipe (36) which removes the mother liquor and wash liquid taken up at the filter (37) from the crystal bed to the fluid register (see number 23 in FIG. 6) and the displacer (38) which serves for maintaining the cross-sectional structure of the crystal bed after the filter (37). In steady-state operation, the wash front is present at a height below the filter (37) in the region of the displacer (38). In order to suppress cooling of the displacer (38) below the wash front, by heat conduction from the warm region below the wash front into the cold region above the wash front, said displacer is preferably made of a heat-insulating material e.g. Teflon. This prevents the displacer (38) from cooling to a temperature below the melting point of the wash medium (=pure product) and the wash medium from crystallizing below the wash front on the displacer (38).

In principle, the filter elements of the drainage pipes can be designed as shown in FIG. 10 and 11 (37, 39, 41), as slot-sieve filters or as perforated-sieve filters (cf. FIG. 11, number 43).

Figure 12:
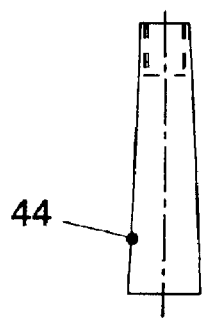
FIG. 12 shows the design of a displacer in the apparatus of FIG. 10.

If the crystals in the crystal bed form a wedge structure poorly accessible for the wash liquid, it may be advantageous to design the displacer, as shown in FIG. 12, number 44 in such a way that it widens conically downward. As a result of this cross-sectional change along the route of the crystal bed, the latter experiences an increasing shear stress, which results in relative movement of the crystals and hence exposure of the crystal wedge for the wash liquid. Otherwise the drainage pipes generally have a constant cross-section.

The filter length is usually from 1 to 3 times the drainage pipe diameter. The concentration zone of the drainage pipe frequently has a length of from 20 to 50 cm. The length of the wash zone is as a rule from 3 to 10 times the distance from the drainage pipe to the jacket of the wash column.

Otherwise, the addresses in FIGS. 5 to 9 attached to this publication have the following meaning:

FIG. 5:
50=oxidation stage 1
51=oxidation stage 2
52=condensation column
53=suspension crystallizer
54=hydraulic wash column
55=heat exchanger for heat of fusion
56=precooler for crude acrylic acid or preheater for recycled mother liquor
57=propene feed
58=air supply 1
59=air supply 2
60=recycle gas having a low acrylic acid content
61=acrylic acid-rich recycle gas
62=waste gas
63=high boiler outlet
64=side take-off for crude acrylic acid
65=precooled crude acrylic acid for suspension crystallization
66=crystal suspension for the hydraulic wash column
67=mother liquor outlet
68=melt circulation for pure acrylic acid product of hydraulic wash column
69=removal of pure acrylic acid product
70=preheated recycled mother liquor FIG. 6:
1=feed of crystal suspension
2=mother liquor removal
3=pure acrylic acid product
4=internal mother liquor stream
5=moving crystal bed
6=wash melt
7=wash column
8=suspension pump
9=heat exchanger for melting the crystals
10=control valve for setting the ratio of wash melt/pure acrylic acid product removal
11=circulation pump of the melt circulation
12=melt circulation
13=pilot pump
14=drainage pipe for mother liquor and wash liquid
15=filter
16=rotor blade for resuspending the washed crystals
17=filtration front (upper limit of crystal bed)
18=Detection of the filtration front (4 optical reflection sensors)
19=wash front (concentration transition pure-impure liquid phase
20=detection of the wash front (4 optical reflection sensors)
21=inhibitor solution (MEHQ in pure acrylic acid product)
22=measuring pump for the inhibitor solution
23=fluid register: collecting tray for mother liquor and wash liquid 24=fluid register: distributor tray for the crystal suspension
25=detection of the wash front (4 temperature sensors)
FIGS. 7 and 8:
As FIG. 6, and additionally:
26=speed of rotor blade (from 10 to 60 rpm)
27=quality control of the pure acrylic acid product (optical extinction measurement at 450 nm)
28=temperature regulation in the melt circulation (14 to 25° C.)
29=4-point position regulation of the wash front (optical position detection)
30=4-point position regulation of the filtration front (optical position detection)
31=4-point position regulation of the wash front (thermal position detection)
FIG. 9:
As for FIG. 7 and 9, and additionally:
32=measurement of the crystal suspension density (crystal fraction of the suspension)
33=measurement of the suspension mass flow
34=ratio regulation (mass of the wash medium =factor×mass of crystals removed)
35=regulation of the wash medium mass flow; setpoint value of 34
FIG. 10 to 12:
36=discharge pipe
37=filter for mother liquor and wash medium; designed here as slot filter
38=displacer made of heat-insulating material (e.g. Teflon); of cylindrical design here
43=filter design with hole geometry
44=displacer in conical design Advantageously, the hydraulic wash column described is operated using pulsating liquid streams. These are streams whose magnitude of the flow rate, but not the flow direction, varies periodically as a function of time. The flow direction is not reversed at any time. They can be realized in a simple manner, for example by periodically varying, as a function of time, either the magnitude of the flow rate of the stream of wash melt fed to the wash column or the magnitude of the flow rate of the stream of mother liquor removed from the wash column. Furthermore, the magnitude of the flow rate of the stream of suspension fed to the wash column can be varied periodically as a function of time.

B) Suitable Wash Columns with Mechanical Transport of the Crystal Bed

Figure 3:
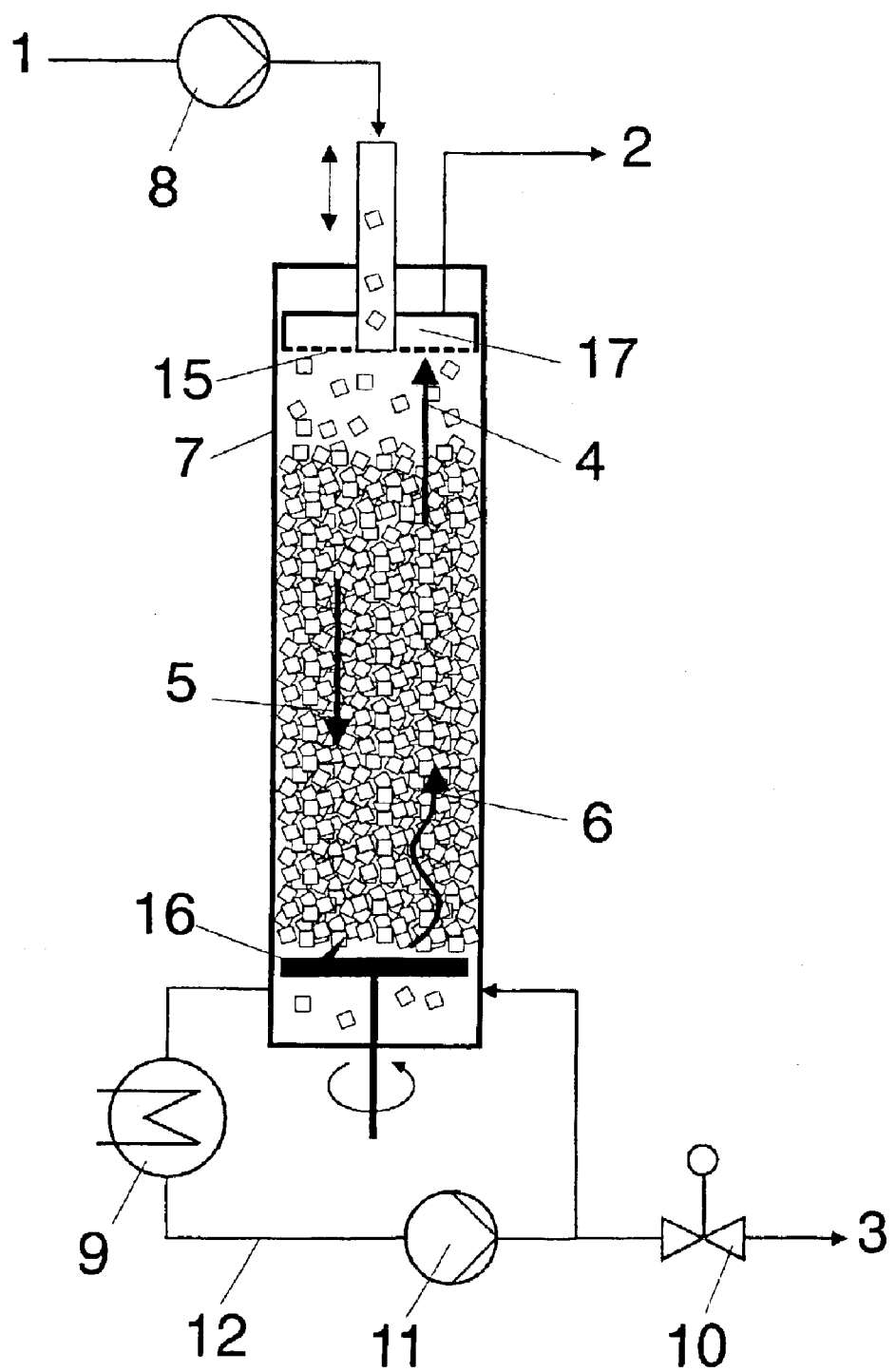
FIGS. 3 and 4 each show a wash column with mechanical bed transport.
Figure 4:
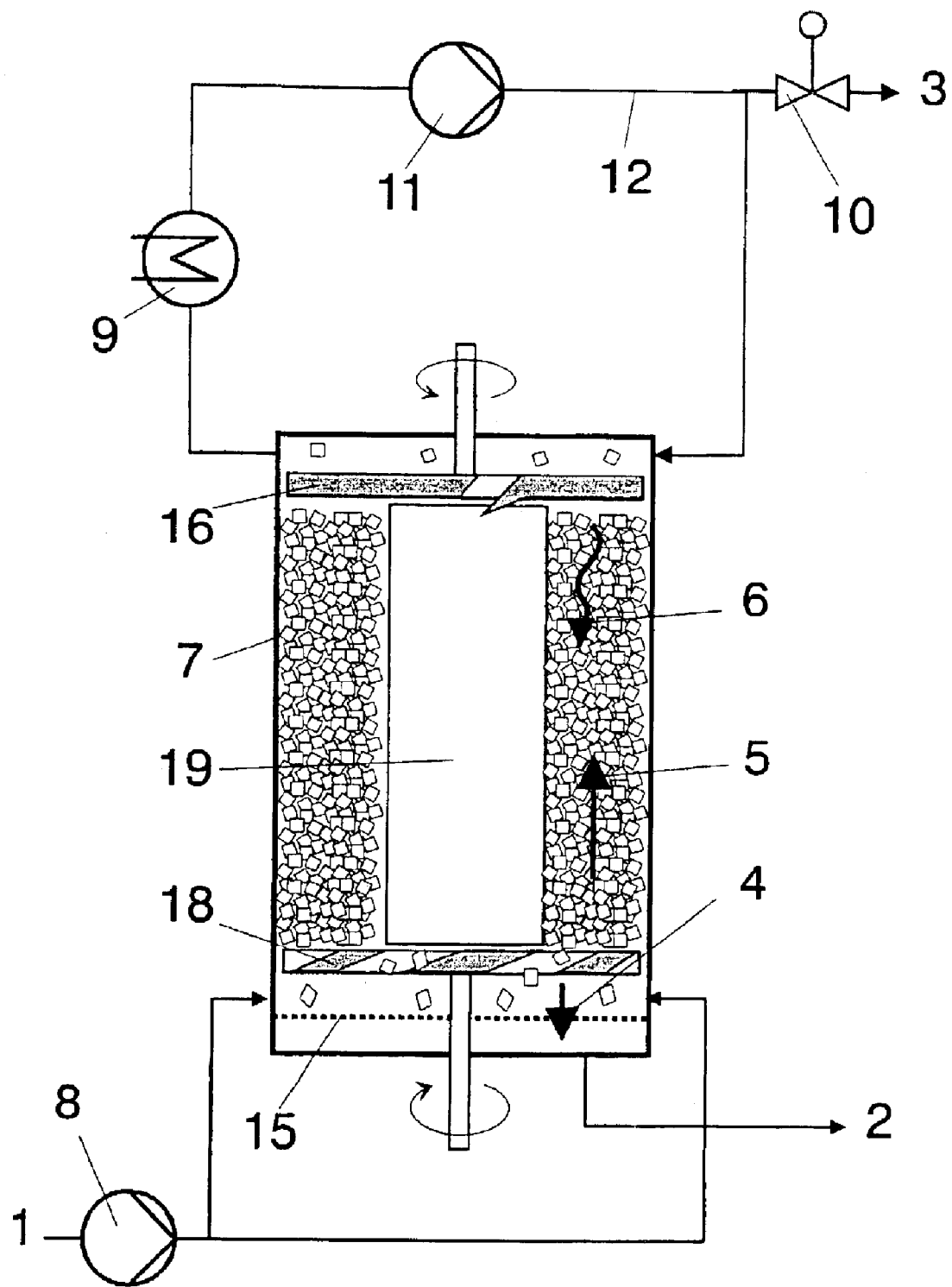

Wash columns suitable for the integration described and having mechanical transport of the crystal bed differ from hydraulic wash columns substantially in that the transport of the crystal bed is effected by mechanical apparatus (for example a screw-blade rotor or an oscillating piston), which is why they contain no drainage pipes. The conventional filter separating off the mother liquor is usually present either in the mechanical transport means (for example in the case of the oscillating piston) or behind the mechanical transport means (for example in the case of the screw-blade rotor). Schematic diagrams of mechanical wash columns suitable for the integration described are shown in FIGS. 3 and 4 attached as an annex to this patent.

The material recommended for the wash columns to be used according to the invention is stainless steel, in particular stainless steel of grade 1.4571. This also applies to the filters.

Polymerization of the pure melt removed from the wash column is inhibited in a manner known per se by adding polymerization inhibitors. In the case of particularly high purity of the acrylic acid crystals present in the crude acrylic acid suspension, the polymerization inhibitor is added in a manner known per se as early as when they are being melted. This can be effected, for example, by a procedure in which the monomethyl ether of hydroquinone is dissolved in pure product melt (acrylic acid) (for example in an amount of up to 1000 ppm by weight or more, based on the solution) and this solution is added during the melting (cf. for example EP-A 776875).

The lowest porosity within the crystal bed in the wash-melt wash column to be used according to the invention is usually $\leq 0.45$, frequently from 0.15 to 0.35.

Figure 2:
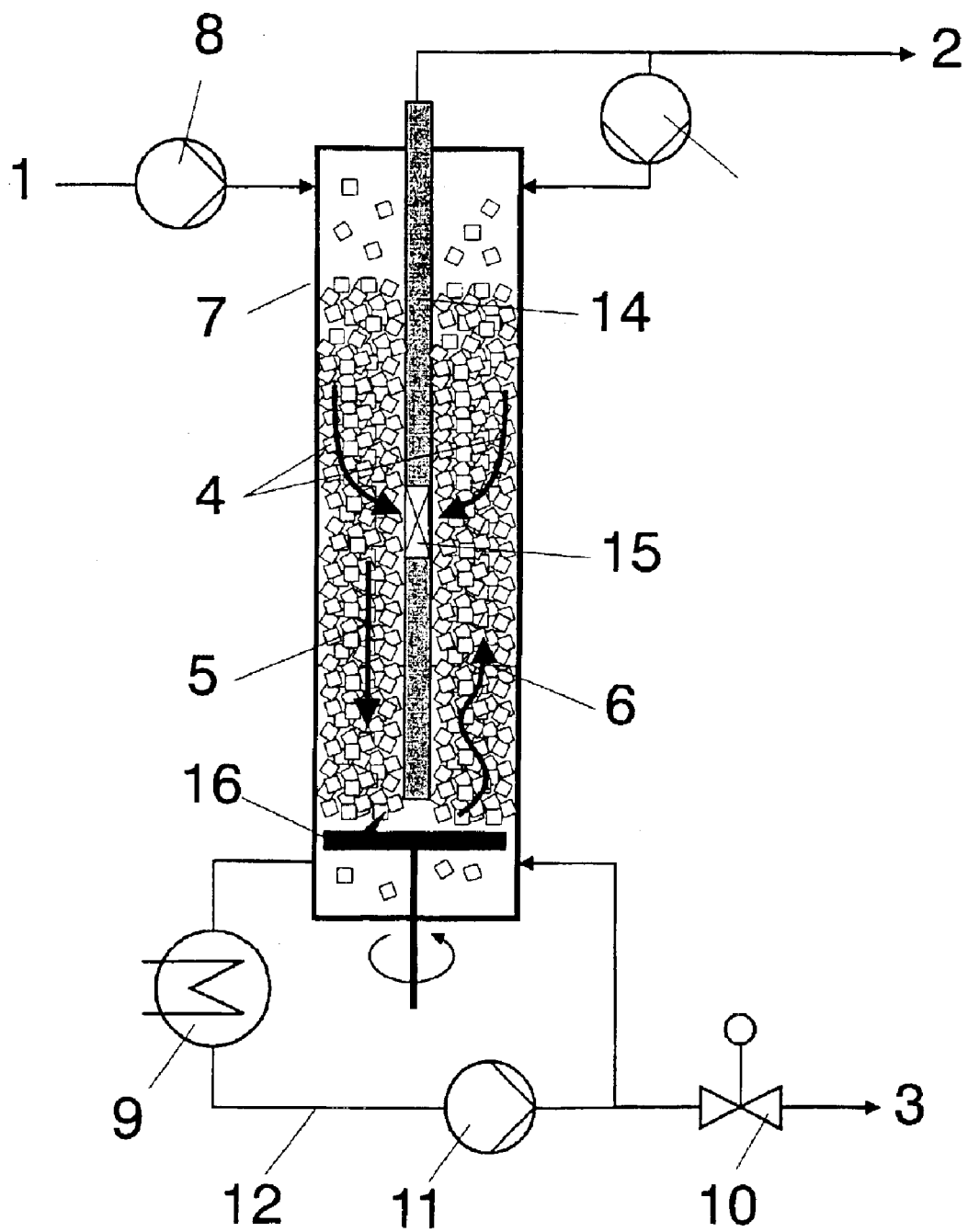
FIG. 2 shows a wash column with hydraulic crystal bed transport.

If, according to the invention, a hydraulic wash-melt wash column is used (for example one according to EP-A 398 437, EP-A 97405 or U.S. Pat. No. 4,735,781 would be suitable as already stated), the hydraulic pressure is as a rule from 0.1 to 10, frequently from 1 to 3 bar. According to the invention, pulsed wash columns can also be used or the wash column can be operated with pulsating streams, as described, for example, in EP-A 97405. As already stated, FIGS. 2 to 4 illustrate the principle of some wash-melt wash columns suitable according to the invention (FIG. 2=hydraulic crystal bed transport, FIGS. 3 and 4=mechanical bed transport and FIG. 1=gravity bed transport).

Here the numerals in these figures have the following meanings:

1: Suspension
2: Residual melt (mother liquor)
3: Product (molten pure crystals)
4: Impure residual melt
5: Moving crystal bed
6: Wash liquid (melt)
7: Wash column
8: Suspension pump
9: Heat exchanger for melting the crystals
10: Control valve for adjusting the ratio of wash liquid (melt) to product
11: Circulation pump of the melt circulation
12: Melt circulation
13: Stirrer
14: Filter tube
15: Filter
16: Rotating knife for resuspending the washed crystals
17: Oscillating piston with filtering end surface and residual melt discharge
18: Skew-blade rotor for transporting the crystal bed
19: Cylindrical displacer

EXAMPLES

Analogously to example 1 of DE-A 19909923, 150 kg/h of a crude acrylic acid having the following composition are produced:

| | |
|---|---|
| Acrylic acid | 98.5% by weight |
| Acetic acid | 0.8% by weight |
| Propionic acid | 500 ppm by weight |
| Furfural | 4800 ppm by weight |
| Maleic anhydride | 40 ppm by weight |
| Benzaldehyde | 680 ppm by weight |
| Water | 1.5% by weight |
| Phenothiazine | 200 ppm by weight |

The crude acrylic acid is fed to a suspension crystallizer. The suspension crystallizer is a cooling-disk crystallizer (100 l internal volume). The heat of crystallization is removed via the cooling surfaces of the container. The equilibrium temperature of the residual melt is 9.5° C. In experiments independent of one another, the crude acrylic acid suspension produced in the crystallization (solids content about 20% by weight) is a) washed in a gravity wash-melt wash column;
b) washed in hydraulic wash-melt wash column;
c) separated batchwise into crystals and mother liquor in a centrifuge (800 g) in a centrifuging time of 30 seconds. The crystals are then washed with molten (previously washed) crystal material (in the mass ratio of 1 part of washing medium to 5 parts of crystal material) for 30 seconds at 800 g.

The reflux ratio (ratio of amount of pure melt removed per unit time to amount of wash melt recycled per unit time) and the temperature difference of the wash column are chosen to be roughly identical. The analysis of the washed crystals is the following for the cases a) to c):

| c): | | | a) and b): | | |
|---|---|---|---|---|---|
| Acrylic acid | 99.6% | by weight | Acrylic acid | 99.8% | by weight |
| Acetic acid | 0.18% | by weight | Acetic acid | 1350 | ppm by weight |
| Propionic acid | 203 | ppm by weight | Propionic acid | 170 | ppm by weight |
| Furfural | 405 | ppm by weight | Furfural | 14 | ppm by weight |
| Maleic anhydride | 1.6 | ppm by weight | Maleic anhydride | no longer detectable | |
| Benzaldehyde | 58 | ppm by weight | Benzaldehyde | no longer detectable | |
| Water | 2700 | ppm by weight | Water | 200 | ppm |
| Phenothiazine | 10 | ppm by weight | Phenothiazine | no longer detectable | |

A better purity is obtained by routes a) and b) than by route c); the results by routes a) and b) are substantially indistinguishable. In particular, the crystalline acrylic acid to be obtained by a) and b) contains less acetic acid.

We claim:

1. A process for purifying a crude acrylic acid melt which contains, on a dry weight basis, $\geq$80% by weight of acrylic acid and, as impurities, at least $\geq$100 ppm by weight of acetic acid and $\geq$10 ppm by weight of propionic acid, which comprises:

performing a suspension crystallization comprising converting a crude acrylic acid melt at low temperatures into a crude acrylic acid suspension which contains acrylic acid crystals, a residual melt and from 0.20 to 10% by weight, based on the weight of the acrylic acid contained in the crude acrylic acid melt, of water, wherein the amount by weight of impurities in the acrylic acid crystals is less than, and the amount by weight of impurities in the residual melt is greater than, the amount by weight of impurities in the crude acrylic acid melt; and passing the crude acrylic acid suspension to a wash column, whereupon the acrylic acid crystals of the remaining crude acrylic acid suspension are separated from remaining residual melt in the wash column, with the proviso that:

a) the wash column is a wash column with forced transport of the acrylic acid crystals therein, and
b) the acrylic acid crystals purified in the wash column are washed by a wash liquid which is a melt of purified acrylic acid crystals.

2. The process as claimed in claim 1, wherein the crude acrylic acid melt contains, on a dry weight basis, $\geq$80% by weight of acrylic acid, from $\geq$100 ppm by weight to $\leq$15% by weight of acetic acid, from $\geq$10 ppm by weight to $\leq$5% by weight of propionic acid, up to 5% by weight of low molecular weight aldehydes, up to 3% by weight of polymerization inhibitors and from 0 to 5% by weight of acrylic acid oligomers.

3. The process as claimed in claim 1, wherein the crude acrylic acid melt contains, on a dry weight basis, $\geq$90% by weight of acrylic acid, from $\geq$100 ppm by weight to $\leq$5% by weight of acetic acid, from $\geq$10 ppm by weight to $\leq$2% by weight of propionic acid, up to 2% by weight of low molecular weight aldehydes, up to 2% by weight of polymerization inhibitors and from 0 to 3% by weight of acrylic acid oligomers (Michael adducts).

4. A process as claimed in claim 1, wherein the crude acrylic acid melt contains, on a dry weight basis, $\geq$95% by weight of acrylic acid, from $\geq$100 ppm by weight to $\leq$3% by weight of acetic acid, from $\geq$10 ppm by weight to $\leq$2% by weight of propionic acid, up to 2% by weight of low molecular weight aldehydes, up to 2% by weight of polymerization inhibitors and from 0 to 2% by weight of acrylic acid oligomers (Michael adducts).

5. The process as claimed in claim 1, wherein the production of the acrylic acid crystals of the crude acrylic acid suspension is effected in the presence of 0.40 to 8% by weight, based on the weight of the acrylic acid that is present in the crude acrylic acid melt, of water.

6. The process as claimed in claim 5, wherein the production of the acrylic acid crystals of the crude acrylic acid suspension is effected in the presence of 0.60 to 5% by weight, based on the weight of the acrylic acid that is present in the crude acrylic acid melt, of water.

7. The process as claimed in claim 6, wherein the production of the acrylic acid crystals of the crude acrylic acid suspension is effected in the presence of 0.60 to 3% by weight, based on the weight of the acrylic acid that is present in the crude acrylic acid melt, of water.

8. The process as claimed in claim 1, wherein the difference between the temperature of the crude acrylic acid suspension fed to the wash column and the temperature of the wash melt recycled to the wash column is from 2 to 15° C.

9. The process as claimed in claim 1, wherein the wash column is a mechanical wash column.

10. The process as claimed in claim 1, wherein the wash column is a hydraulic wash column.

11. The process as claimed in claim 8, wherein the difference between the temperature of the crude acrylic acid suspension fed to the wash column and the temperature of the wash melt recycled to the wash column is from 2 to 4° C.

12. The process as claimed in claim 8, wherein the crude acrylic acid suspension is formed with an acrylic acid crystal content of 10 to 80% by weight, based on the total weight of the crude acrylic acid suspension.

13. The process as claimed in claim 8, wherein the crude acrylic acid suspension is formed with an acrylic acid crystal content of 20 to 60% by weight, based on the total weight of the crude acrylic acid suspension.

14. The process as claimed in claim 8, wherein from 70 to 80% by weight of the acrylic acid crystals that are withdrawn from the wash column to form a melt is withdrawn as purified acrylic acid product.

15. The process as claimed in claim 1, which further comprises: mechanically separating a portion of the residual melt from the crude acrylic acid suspension after converting the crude acrylic acid melt into a crude acrylic acid suspension.

16. The process as claimed in claim 15, wherein the crude acrylic acid melt contains, on a dry weight basis,
≧80% by weight of acrylic acid,
from ≧100 ppm by weight to ≦15% by weight of acetic acid,
from ≧10 ppm by weight to ≦5% by weight of propionic acid,
up to 5% by weight of low molecular weight aldehydes,
up to 3% by weight of polymerization inhibitors and
from 0 to 5% by weight of acrylic acid oligomers.

17. The process as claimed in claim 15, wherein the crude acrylic acid melt contains, on a dry weight basis,
≧90% by weight of acrylic acid,
from ≧100 ppm by weight to ≦5% by weight of acetic acid,
from ≧10 ppm by weight to ≦2% by weight of propionic acid,
up to 2% by weight of low molecular weight aldehydes,
up to 2% by weight of polymerization inhibitors and
from 0 to 3% by weight of acrylic acid oligomers (Michael adducts).

18. A process as claimed in claim 15, wherein the crude acrylic acid melt contains, on a dry weight basis,
≧95% by weight of acrylic acid,
from ≧100 ppm by weight to ≦3% by weight of acetic acid,
from ≧10 ppm by weight to ≦2% by weight of propionic acid,
up to 2% by weight of low molecular weight aldehydes,
up to 2% by weight of polymerization inhibitors and
from 0 to 2% by weight of acrylic acid oligomers (Michael adducts).

19. The process as claimed in claim 15, wherein the production of the acrylic acid crystals of the crude acrylic acid suspension is effected in the presence of 0.40 to 8% by weight, based on the weight of the acrylic acid that is present in the crude acrylic acid melt, of water.

20. The process as claimed in claim 19, wherein the production of the acrylic acid crystals of the crude acrylic acid suspension is effected in the presence of 0.60 to 5% by weight, based on the weight of the acrylic acid that is present in the crude acrylic acid melt, of water.

21. The process as claimed in claim 20, wherein the production of the acrylic acid crystals of the crude cyclic acid suspension is effected in the presence of 0.60 to 3% by weight, based on the weight of the acrylic acid that is present in the crude acrylic acid melt, of water.

22. The process as claimed in claim 15, wherein the difference between the temperature of the crude acrylic acid suspension fed to the wash column and the temperature of the wash melt recycled to the wash column is from 2 to 15° C.

23. The process as claimed in claim 15, wherein the wash column is a mechanical wash column.

24. The process as claimed in claim 15, wherein the wash column is a hydraulic wash column.

25. The process as claimed in claim 22, wherein the difference between the temperature of the crude acrylic acid suspension fed to the wash column and the temperature of the wash melt recycled to the wash column is from 2 to 4° C.

26. The process as claimed in claim 22, wherein the crude acrylic acid suspension is formed with an acrylic acid crystal content of 10 to 80% by weight, based on the total weight of the crude acrylic acid suspension.

27. The process as claimed in claim 22, wherein the crude acrylic acid suspension is formed with an acrylic acid crystal content of 20 to 60% by weight, based on the total weight of the crude acrylic acid suspension.

28. The process as claimed in claim 22, wherein from 70 to 80% by weight of the acrylic acid crystals that are withdrawn from the wash column to form a melt is withdrawn as purified acrylic acid product.

29. The process as claimed in claim 8, wherein the difference between the temperature of the crude acrylic acid suspension fed to the wash column and the temperature of the wash melt recycled to the wash column is from 2 to 10° C.

30. The process as claimed in claim 8, wherein from 80 to 100% by weight of the acrylic acid crystals that are withdrawn from the wash column to form a melt is withdrawn as purified acrylic acid product.

31. The process as claimed in claim 22, wherein the difference between the temperature of the crude acrylic acid suspension fed to the wash column and the temperature of the wash melt recycled to the wash column is from 2 to 10° C.

32. The process as claimed in claim 22, wherein from 80 to 100% by weight of the acrylic acid crystals that are withdrawn from the wash column to form a melt is withdrawn as purified acrylic acid product.

33. The process as claimed in claim 1, wherein the crude acrylic acid suspension has an acrylic acid crystal content of 10 to 80% by weight.

34. The process as claimed in claim 33, wherein the crude acrylic acid suspension has an acrylic acid crystal content of 20 to 60% by weight.

35. The process as claimed in claim 34, wherein the crude acrylic acid suspension has an acrylic acid crystal content of 30 to 50% by weight.

36. The process as claimed in claim 2, wherein the polymerization inhibitor is dibenzo-1,4-thiazine, 4-hydroxy-2,2,6,6-tetramethylpiperidin-1-oxyl and/or p-methoxyphenol.

37. The process as claimed in claim 33, wherein the polymerization inhibitor is dibenzo-1,4-thiazine, 4-hydroxy-2,2,6,6-tetramethylpiperidin-1-oxyl and/or p-methoxyphenol.

38. The process as claimed in claim 4, wherein the polymerization inhibitor is dibenzo-1,4-thiazine, 4-hydroxy-2,2,6,6-tetramethylpiperidin-1-oxyl and/or p-methoxyphenol.

39. The process as claimed in claim 16, wherein the polymerization inhibitor is dibenzo-1,4-thiazine, 4-hydroxy-2,2,6,6-tetramethylpiperidin-1-oxyl and/or p-methoxyphenol.

40. The process as claimed in claim 17, wherein the polymerization inhibitor is dibenzo-1,4-thiazine, 4-hydroxy-2,2,6,6-tetramethylpiperidin-1-oxyl and/or p-methoxyphenol.

41. The process as claimed in claim 18, wherein the polymerization inhibitor is dibenzo-1,4-thiazine, 4-hydroxy- 2,2,6,6-tetramethylpiperidin-1-oxyl and/or p-methoxyphenol.

42. The process as claimed in claim 1, wherein the acrylic acid crystals, as geometrical bodies, have a length:width:height ratio of 1 to 5:1:1 wherein the length ranges from 10 to 100 μm.

43. The process as claimed in claim 1, wherein the acrylic acid crystals, as geometrical bodies, have a length:width:height ratio of 1 to 5:1:1 wherein the length ranges from 100 to 800 μm.

44. The process as claimed in claim 1, wherein the acrylic acid crystals, as geometrical bodies, have a length:width:height ratio of 1 to 5:1:1 wherein the length ranges from 100 up to 400 μm.

45. The process as claimed in claim 15, wherein the acrylic acid crystals, as geometrical bodies, have a length:width:height ratio of 1 to 5:1:1 wherein the length ranges from 10 to 100 μm.

46. The process as claimed in claim 15, wherein the acrylic acid crystals, as geometrical bodies, have a length:width:height ratio of 1 to 5:1:1 wherein the length ranges from 100 to 800 μm.

47. The process as claimed in claim 15, wherein the acrylic acid crystals, as geometrical bodies, have a length:width:height ratio of 1 to 5:1:1 wherein the length ranges from 100 up to 400 μm.

* * * * *